US012702326B2

(12) United States Patent
Ericson et al.

(10) Patent No.: US 12,702,326 B2
(45) Date of Patent: Aug. 11, 2026

(54) STROKE DETECTION SENSOR

(71) Applicant: Uman Sense AB, Lund (SE)

(72) Inventors: Petter Ericson, Limhamn (SE); Johan Wasselius, Lund (SE); Karl Astrom, Lund (SE); Rikard Berthilsson, Furulund (SE)

(73) Assignee: UMAN SENSE AB, Lund (SE)

( * ) Notice: Subject to any disclaimer, the term of this patent is extended or adjusted under 35 U.S.C. 154(b) by 1139 days.

(21) Appl. No.: 17/415,183

(22) PCT Filed: Dec. 19, 2019

(86) PCT No.: PCT/SE2019/051322
§ 371 (c)(1),
(2) Date: Jun. 17, 2021

(87) PCT Pub. No.: WO2020/130924
PCT Pub. Date: Jun. 25, 2020

(65) Prior Publication Data

US 2022/0061738 A1 Mar. 3, 2022

(30) Foreign Application Priority Data

Dec. 20, 2018 (GB) ..................................... 1820892
Nov. 12, 2019 (SE) ..................................... 193037-0

(51) Int. Cl.
*A61B 5/11* (2006.01)
*A61B 5/00* (2006.01)
(Continued)

(52) U.S. Cl.
CPC ................ *A61B 5/11* (2013.01); *A61B 5/162* (2013.01); *A61B 5/4064* (2013.01);
(Continued)

(58) Field of Classification Search
None
See application file for complete search history.

(56) References Cited

U.S. PATENT DOCUMENTS 6,301,964 B1 10/2001 Fyfe et al.
6,703,939 B2 3/2004 Lehrman et al.
(Continued)

FOREIGN PATENT DOCUMENTS

EP 2708185 B1 4/2017
EP 3154627 B1 4/2018
(Continued)

OTHER PUBLICATIONS

International Search Report issued on Mar. 17, 2020 in International Application No. PCT/SE2019/051322.
(Continued)

*Primary Examiner* — Aurelie H Tu
(74) *Attorney, Agent, or Firm* — Harness, Dickey & Pierce, P.L.C.

(57) ABSTRACT

A stroke detection apparatus for determining that a stroke is occurring or has recently occurred to a user, wherein the apparatus comprises a data processing device comprising a processor and at least one wearable sensor configured to be worn by a user and configured to transmit a movement data of the user to the data processing device. The data processing device is configured to process the movement data to determine a first probability of a user stroke over a first time period and a second probability of a user stroke over a second time period. A stroke detection signal is then generated in dependence on at least the first probability and second probability.

8 Claims, 10 Drawing Sheets

(51) Int. Cl.
*A61B 5/16* (2006.01)
*G16H 40/67* (2018.01)

(52) U.S. Cl.
CPC ............ *A61B 5/4094* (2013.01); *A61B 5/681* (2013.01); *A61B 5/6824* (2013.01); *A61B 5/6828* (2013.01); *A61B 5/7275* (2013.01); *A61B 5/747* (2013.01); *A61B 5/7475* (2013.01); *G16H 40/67* (2018.01)

(56) References Cited

U.S. PATENT DOCUMENTS 6,836,744 B1 12/2004 Asphahani et al.
7,203,541 B2 4/2007 Sowelam et al.
7,421,369 B2 9/2008 Clarkson
7,503,900 B2 3/2009 Goswami
7,516,038 B2 4/2009 Lehtonen et al.
7,753,861 B1 7/2010 Kahn et al.
7,878,990 B2 2/2011 Al-Obaidi et al.
7,921,716 B2 4/2011 Morris Bamberg et al.
7,974,689 B2 7/2011 Volpe et al.
7,981,058 B2 7/2011 Akay
8,011,229 B2 9/2011 Lieberman et al.
8,032,199 B2 10/2011 Linti et al.
8,060,337 B2 11/2011 Kulach et al.
8,187,209 B1 5/2012 Giuffrida
8,204,710 B2 6/2012 Walthert
8,409,116 B2 4/2013 Wang et al.
8,608,671 B2 12/2013 Kinoshita et al.
8,715,208 B2 5/2014 Hodgins et al.
8,738,118 B2 5/2014 Moon et al.
8,801,636 B2 8/2014 Lewicke et al.
8,909,330 B2 12/2014 McCombie et al.
8,961,439 B2 2/2015 Yang et al.
8,968,218 B2 3/2015 Wukasch et al.
9,060,714 B2 6/2015 Bajcsy et al.
9,107,615 B2 8/2015 Buckman
9,173,596 B1 11/2015 Berme et al.
9,179,862 B2 11/2015 Stergiou et al.
9,186,096 B2 11/2015 Solinsky
9,265,448 B2 2/2016 Bonnet
9,314,394 B2 4/2016 Hirata et al.
9,375,570 B2 6/2016 Kiani et al.
9,392,966 B2 7/2016 Ten Kate
9,445,720 B2 9/2016 Janna et al.
9,554,731 B2 1/2017 Malchau et al.
9,591,993 B2 3/2017 Morris Bamberg et al.
9,723,987 B2 8/2017 Goetz
9,802,040 B2 10/2017 Ichimura et al.
9,826,921 B2 11/2017 Griffiths et al.
9,877,523 B2 1/2018 Ellis
9,877,668 B1 1/2018 Sarkar et al.
9,901,290 B2 2/2018 Najafi et al.
9,936,912 B2 4/2018 Roovers et al.
9,974,478 B1 5/2018 Brokaw et al.
9,993,181 B2 6/2018 Ross
10,026,292 B2 7/2018 Baker et al.
2005/0240086 A1 10/2005 Akay
2007/0076270 A1 4/2007 Poletto
2007/0276270 A1 11/2007 Tran
2009/0062696 A1 3/2009 Nathan et al.
2009/0137921 A1 5/2009 Kramer et al.
2009/0227890 A1* 9/2009 Lanfermann ........ A61B 5/4824 600/555
2009/0319221 A1* 12/2009 Kahn .................... G06F 3/0346 702/141
2011/0190593 A1 8/2011 McNair
2011/0245629 A1 10/2011 Giftakis et al.
2012/0215076 A1 8/2012 Yang et al.
2013/0060167 A1 3/2013 Dracup et al.
2013/0154827 A1 6/2013 Housley
2013/0218053 A1 8/2013 Kaiser et al.
2014/0039274 A1 2/2014 Sarrafzadeh et al.
2014/0249452 A1 9/2014 Marsh et al.
2015/0018723 A1 1/2015 Lee et al.
2015/0099945 A1 4/2015 Hawkins, III et al.
2015/0157252 A1 6/2015 Sabesan
2015/0164377 A1 6/2015 Nathan et al.
2015/0272511 A1 10/2015 Najafi et al.
2016/0038059 A1 2/2016 Asada et al.
2016/0038061 A1 2/2016 Kechichian et al.
2016/0058324 A1* 3/2016 Cao ...................... A61B 5/7282 600/302
2016/0058326 A1 3/2016 Winfree et al.
2016/0166202 A1 6/2016 Haraikawa et al.
2016/0213318 A1 7/2016 Parodi et al.
2016/0263437 A1 9/2016 Kow et al.
2016/0278666 A1 9/2016 Kozloski et al.
2016/0278708 A1 9/2016 Vrazic
2016/0296156 A1 10/2016 Conradsen et al.
2016/0310069 A1 10/2016 Sinderby et al.
2016/0317040 A1 11/2016 Russell et al.
2016/0324445 A1 11/2016 Kim et al.
2016/0331255 A1* 11/2016 Cheatham, III ....... A61B 5/024
2017/0007168 A1 1/2017 Mirelman et al.
2017/0042453 A1 2/2017 Cheung
2017/0042467 A1 2/2017 Herr et al.
2017/0055880 A1 3/2017 Agrawal et al.
2017/0146386 A1* 5/2017 Wiard .................. A61B 5/7282
2017/0150897 A1 6/2017 Komaki
2017/0156662 A1 6/2017 Goodall et al.
2017/0188895 A1 7/2017 Nathan
2017/0195637 A1 7/2017 Kusens et al.
2017/0202724 A1 7/2017 De Rossi et al.
2017/0231533 A1 8/2017 Qu et al.
2017/0273616 A1 9/2017 Yang et al.
2017/0281054 A1 10/2017 Stever et al.
2017/0291065 A1 10/2017 Klopman
2017/0325749 A1* 11/2017 Shah ................... A61B 5/7275
2017/0352240 A1 12/2017 Carlton-Foss
2018/0028105 A1 2/2018 Osorio
2018/0049671 A1 2/2018 Markison et al.
2018/0125386 A1 5/2018 Lim et al.
2018/0140842 A1 5/2018 O Laighin et al.
2018/0146910 A1 5/2018 De Vries et al.
2018/0146914 A1 5/2018 Snow et al.
2018/0153477 A1 6/2018 Nagale et al.
2018/0177436 A1 6/2018 Chang et al.
2018/0220932 A1 8/2018 Jung
2018/0249967 A1 9/2018 Lederman et al.
2018/0279966 A1 10/2018 Park et al.
2018/0317811 A1 11/2018 Lee et al.
2019/0029606 A1* 1/2019 Sheth .................. A61B 5/7275
2021/0106238 A1 4/2021 Strasser et al.
2021/0196182 A1* 7/2021 D'Arcy .................... A61B 5/16
2021/0202090 A1* 7/2021 O'Donovan ............ G10L 25/66

FOREIGN PATENT DOCUMENTS

EP 3308912 A1 4/2018
EP 2445405 B1 6/2018
WO WO-2006134359 A1 12/2006
WO WO-13/045725 A2 4/2013
WO WO-2013/056099 A1 4/2013
WO WO-2016/172557 A1 10/2016
WO WO-2017/123725 A1 7/2017
WO WO-2017/202839 A1 11/2017
WO WO-18/102579 A1 6/2018
WO WO-2018/110925 A1 6/2018

OTHER PUBLICATIONS

Written Opinion issued on Mar. 17, 2020 in International Application No. PCT/SE2019/051322.
José R. Villar, et al., "A hybrid intelligent recognition system for the early detection of strokes," Integrated Computer-Aided Engineering, pp. 215-277, Jun. 2015.

* cited by examiner

STROKE DETECTION SENSOR

CROSS-REFERENCE TO RELATED APPLICATIONS

This application is the National Phase under 35 U.S.C. § 371 of PCT international application no. PCT/SE2019/051322, filed on Dec. 19, 2019, which claims priority to Great Britain Patent Application No. 1820892.6, filed Dec. 20, 2018, and Swedish Patent Application No. 1930370-0, filed Nov. 12, 2019, the entire contents of each of which are incorporated herein by reference.

TECHNICAL FIELD

The present invention relates to apparatus and methods for detecting stroke in a patient.

BACKGROUND ART

A stroke is a medical condition in which poor blood flow to the brain results in cell death. There are two main causes for stroke. An ischemic stroke is typically caused by a lack of blood flow to parts of the brain resulting from a blockage in an artery that supplies blood to the brain. The blood normally delivers oxygen and nutrients to the brain. Once the oxygen and nutrients are cut off by the blockage, the brain cells cannot make enough energy and will eventually stop working. If the blockage is not cleared, the brain cells will eventually die. A hemorrhagic stroke is cause by bleeding in the brain. The bleeding is typically caused by a damaged blood vessel leaking blood. A hemorrhagic stroke may also be caused by a burst brain aneurism. In both cases, the blood spreads into the surrounding brain tissue causing increased pressure, limiting the operating of the brain cells and eventually damaging the brain tissue.

In both of the above types of stroke, the resultant effect is a change in the function of the brain, as brain cells cease to function correctly. This change can be observed through physical symptoms such as an inability to move or feel on one side of the body, problems communicating, and loss of vision. These physical symptoms often appear more or less immediately after the stroke has begun.

Historically, a stroke was very difficult to treat. Although the patient's symptoms might be recognised and diagnosed as a stroke, limited treatment was available. Where the stroke was identified as an ischemic stroke, a clot-dissolving drug such as a tissue plasminogen activator was given to the patient intravenously, in the hope that the drug would reach the clot and dissolve it sufficiently to allow blood flow to resume through the affected artery. Such a treatment would need to be successfully applied within just a few hours of the start of the stroke to ensure that the damage to the brain tissue was limited. Some studies suggest that the time window for getting the best results from clot-dissolving drug is three hours from the first signs of the stroke.

Where a stroke was not successfully treated, damage to brain tissue became inevitable and the only recourse was to provide the patient with care and rehabilitation training.

More recently, ischemic strokes have been successfully treated via an endovascular procedure called 'mechanical thrombectomy' in which the blood clot is removed by sending a clot retrieval device to the site of the blocked blood vessel in the brain. The device secures the clot and pulls the clot back out the blood vessel as the device is removed. Similarly, hemorrhagic strokes may also be treated via an endovascular procedure by delivering a metal clip to the damaged blood vessel or ruptured aneurysm. The clip is secured to restrict the blood flood and prevent further blood from leaking into the surrounding blood tissue. As with the clot-dissolving drug, significant damage mitigation can be achieved if the procedure is performed within a few hours of the first signs of the stroke.

Therefore, given improved treatment options for ischemic strokes, the importance of recognising and characterising the symptoms of a stroke has increased. For patients with a high risk of suffering a stroke, a method is needed of providing constant monitoring with rapid diagnosis of a stroke and escalation to a health care provider.

There are known techniques for early detection of stroke in patients employing the use of sensors worn on the patient's body. Villar. J R. "A hybrid intelligent recognition system for the early detection of strokes" describes the use of a wearable device that generates warning alarms and automatically connects to e-health services when a stroke is detected. The described approach employs two wearable devices to monitor movement data and employs genetic fuzzy finite-state machines and Time Series (TS) analysis to determine a stroke.

US patent application 2018153477 discloses a device for monitoring patients for a stroke via several sensors for determining 'physiological signals'. The physiological signals may comprise a heart rate signal, an atrial rate signal, a heart rate variability signal, a blood pressure signal, a blood pressure variability signal, a heart sound signal, etc.

U.S. Pat. No. 7,981,058 discloses a device for monitoring patients using low cost biaxial motion sensors. The first sensor captures objective acceleration data, and the second biaxial sensor captures subjective acceleration data relative to at least the first accelerometer. Acceleration data is then used to determine nonlinear parameters and to generate at least two levels of motor function information.

US2017281054 is a US application disclosing a device for monitoring patients for a stroke via a plurality of motion sensors located at one or more anatomical locations on a patient's body and configured to detect a plurality of motion parameters corresponding to a motion of a portion of the patient's body. The motion of the portion of the patient's body is then based on a plurality of predetermined motion sentence features.

US2015157252 is a US application disclosing a device for monitoring patients via several sensors. A technique is described for switching between sensors to determine which sensor is providing the best indication of a physiological signal status of the patient.

However, problems associated with the above systems include problems related to producing a reliable signal indicative of a patient stroke without trigger too many false positives. What is needed is a system capable of generating a stroke detection signal with minimal false positives, and where false positives do occur, the system can graceful handle them without too much inconvenience to the user.

SUMMARY

It is an objective of the invention to at least partly overcome one or more of the above-identified limitations of the prior art.

One or more of these objectives, as well as further objectives that may appear from the description below, are at least partly achieved by means of a method for data processing, a computer readable medium, devices for data processing, and an apparatus according to the independent claims, embodiments thereof being defined by the dependent claims.

One embodiment of the disclosure describes a stroke detection apparatus comprising a data processing device comprising a processor, at least one wearable sensor configured to be worn by a user and configured to transmit a movement data of the user to the data processing device, the data processing device configured to process the movement data to determine a first probability of a user stroke over a first time period and a second probability of a user stroke over a second time period, and generate a stroke detection signal in dependence on at least the first probability and second probability.

Another embodiment of the disclosure describes a method for generating a stroke detection signal comprising: generating, using at least one wearable sensor device configured to be worn by a user, a movement data of the user, transmitting the movement data to a processing device, processing the movement data at a processing device to determine a first probability of a user stroke over a first time period and a second probability of a user stroke over a second time period, generating a stroke detection signal in dependence on at least the first probability and second probability.

BRIEF DESCRIPTION OF DRAWINGS

Embodiments of the invention will now be described in more detail with reference to the accompanying schematic drawings.

DETAILED DESCRIPTION OF EMBODIMENTS

Figure 1:
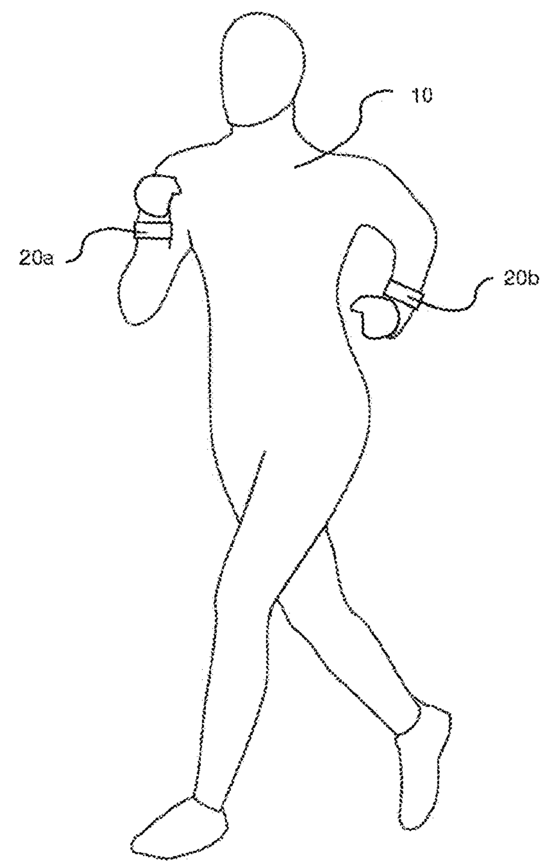
FIG. 1 is a schematic diagram showing a patient wearing a multi-sensor stroke detection apparatus.

The present invention relates to wearable sensors and the use of techniques for providing monitoring and detection of patient conditions, as well as escalation of the patient condition where needed. Throughout the description the same reference numerals are used to identify corresponding elements.

FIG. 1 is schematic diagram showing a patient 10 with a stroke detection apparatus 100 comprising a plurality of wearable sensors 20. In FIG. 1, wearable sensors 20*a*, 20*b* are attached to the patient's wrists. In other embodiments, wearable sensors may be worn on the ankles, either as an alternative to the wrists or in combination with the wrists. Other positions in which the wearable sensors may be warn include footwear, headwear, as well as attached to clothing such as trousers, and upper body garments.

Figure 2:
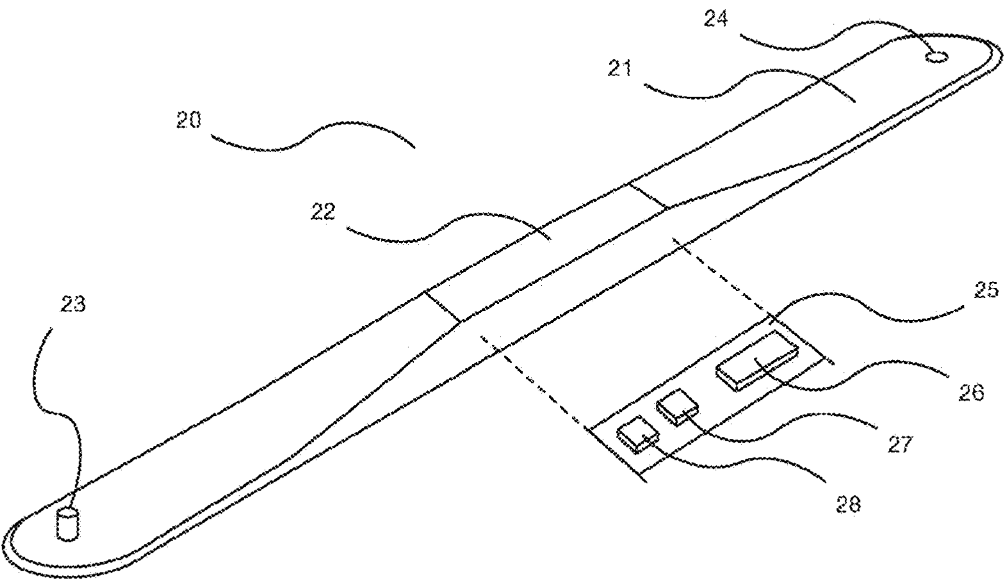
FIG. 2 shows a perspective view of stroke detection apparatus according to an embodiment of the present application.

FIG. 2 shows an embodiment of a wearable sensor 20. In one embodiment, the wearable sensor 20 comprises a strap 21 configured to secure the wearable sensor 20 to the patient, sensor body 22 housing processing board 25. Processing board may comprise power source 26, data processing device 27, and sensor package 28. Sensor package 28 may include any suitable sensor component configured to measure an inclination, a position, an orientation, and/or an acceleration of the part of the patient's body where the wearable sensor 20 is attached. Sensor package 28 may comprise a piezoelectric, piezoresistive and/or capacitive component to convert the mechanical motion into an electrical signal. A piezoceramics (e.g. lead zirconate titanate) or single crystals (e.g. quartz, tourmaline) may be used. Preferably, capacitive accelerometers are employed due to their superior performance in the low frequency range.

The data processing device 27 may be implemented by special-purpose software (or firmware) run on one or more general-purpose or special-purpose computing devices, such as hardware processor(s). Each "element" or "means" of such a computing device refers to a conceptual equivalent of a method step; there is not always a one-to-one correspondence between elements/means and particular pieces of hardware or software routines. One piece of hardware sometimes comprises different means/elements. For example, a processing unit serves as one element/means when executing one instruction, but serves as another element/means when executing another instruction. In addition, one element/means may be implemented by one instruction in some cases, but by a plurality of instructions in some other cases. Such a software-controlled computing device may include one or more processing units, e.g. a CPU ("Central Processing Unit"), a DSP ("Digital Signal Processor"), an ASIC ("Application-Specific Integrated Circuit"), discrete analog and/or digital components, or some other programmable logical device, such as an FPGA ("Field Programmable Gate Array"). The data processing device 27 may further include a system memory and a system bus that couples various system components including the system memory to the processing unit. The system bus may be any of several types of bus structures including a memory bus or memory controller, a peripheral bus, and a local bus using any of a variety of bus architectures. The system memory may include computer storage media in the form of volatile and/or non-volatile memory such as read only memory (ROM), random access memory (RAM) and flash memory. The special-purpose software may be stored in the system memory, or on other removable/non-removable volatile/non-volatile computer storage media which is included in or accessible to the computing device, such as magnetic media, optical media, flash memory cards, digital tape, solid state RAM, solid state ROM, etc. The special-purpose software may be provided to the data processing device 27 on any suitable computer-readable medium, including a record medium and a read-only memory.

The data processing device 27 includes one or more communication interfaces, such as a serial interface, a USB interface, a wireless interface, etc, as well as one or more data acquisition devices, such as an ND converter. In one example, the data processing device 27 may include a transmitter component configured to send sensor data received from the sensor package 28 and processed by the data processing device 27 and/or ND converter over the one or more communication interfaces. In one embodiment, a communication interface is provided via a Bluetooth® or WiFi transceiver and the processed sensor data is sent to a control device 30 (described below). The processed sensor data may alternatively be sent to one or more remote devices via a GSM, LTE, or similar mobile communications interface.

Power source 26 may comprise a battery, kinetic energy source, or other power source suitable for a wearable device. The power source 26 is arranged to provide an energy source for powering the data processing device 27 and sensor package 28 of the processing board 25.

Figure 3:
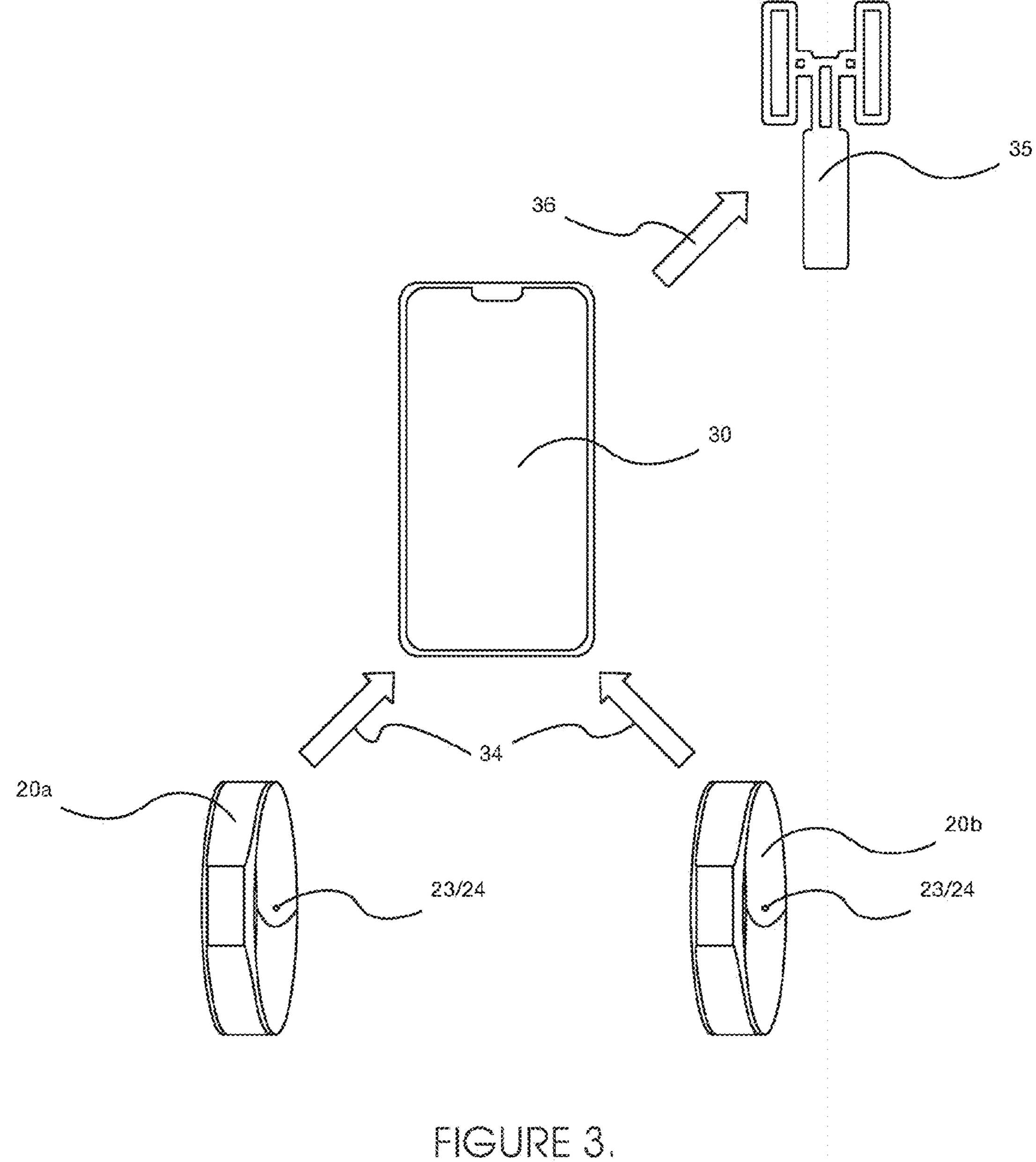
FIG. 3 is a schematic diagram of a stroke detection apparatus according to an embodiment of the present application.

Wearable sensor 20 may further comprise a fastening component 23 configured to be secured with a counterpart component 24, to allow the device to be secured to a limb of patient 10. In one embodiment, the fastening component 23 comprises a sensor configured to determine whether the strap 21 of wearable sensor 20 is in an 'open' configuration or a 'secured' configuration. An example of an 'open' configuration of the strap is shown in FIG. 2 where the wearable sensor 20 is not secured to anything. An example of the 'closed' configuration is shown in FIG. 1 where the wearable sensor 20 is secured to the patient. Similarly, an example of the 'closed' configuration is shown in FIG. 3, where the fastening component 23 has been fastened to counterpart component 24 to arrange the strap of wearable sensor 20 in a secured loop. In one embodiment, the sensor of fastening component 23 is electrically connected to processing board 25 such that data processing device 27 may determine the configuration of the strap 21 of wearable sensor 20.

Wearable sensor 20 may further comprise a feedback mechanism comprising at least one of a vibration motor or equivalent physical actuator, a light source, e.g., an LED, or sound source, e.g., a speaker. The feedback mechanism may be configured to generate one of a vibration prompt, a visual prompt, or an audible prompt, capable of attracting a healthy patient's attention.

FIG. 3 shows an example wireless network according to an embodiment of the present application. In FIG. 3, two wearable sensors 20, shown as 20*a* and 20*b*, are worn by a patient (not shown) and the respective strap 21 of each wearable sensor is in the 'closed' configuration. Each wearable sensors 20*a*, 20*b* collects sensor data from the patient, process said data, and transmit the data to the control device 30 via wireless networking interface 34. This process is described in greater detail below and with reference to FIG. 4*a*. Control device 30 may be a mobile phone device such an Apple™ iPhone™, iPad™, Apple Watch™, Android™ device, Wear OS™ device, Laptop device, or similar. Control device 30 receives the data from the wearable sensors, processes it, determines a patient condition, and executes an escalation process where appropriate. This process is described in greater detail below and with reference to FIG. 4*b*.

Figure 4A:
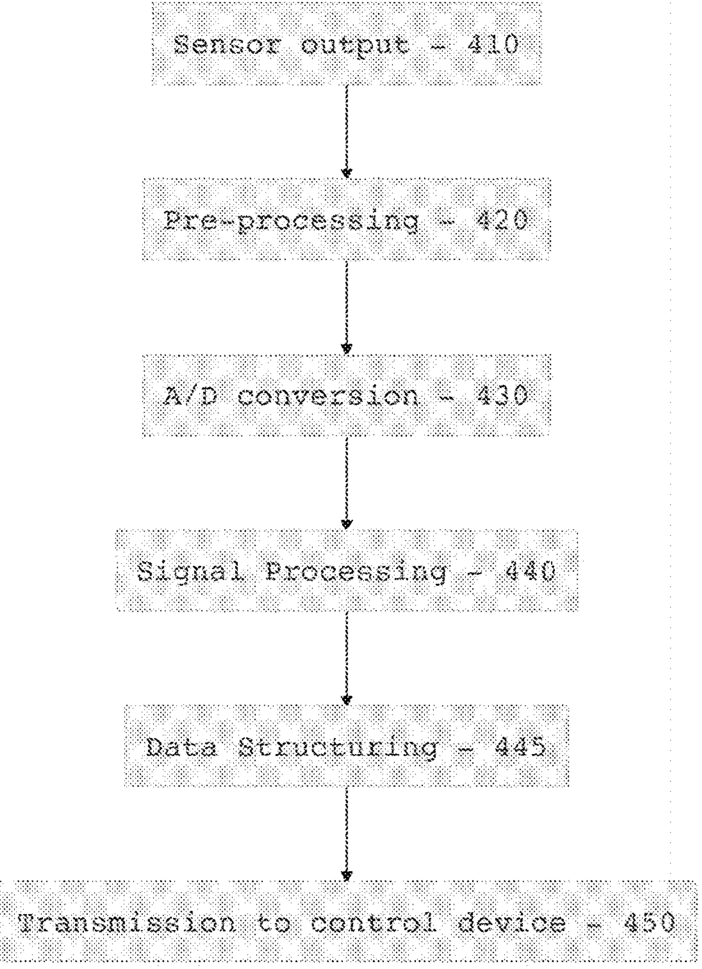
FIG. 4*a* and FIG. 4*b* are process flow diagrams showing execution flow of the wearable sensor and control device respectively.

FIG. 4*a* shows an embodiment of the process flow for data processing device 27. The process flow shown in FIG. 4*a* may be executed in a continuous loop or periodically. Where the process is executed periodically, an energy saving mode may be employed between executions to minimise battery usage.

In step 410, sensor output is received by data processing device 27 from sensor package 28. Where the sensor data is generated by e.g. a piezoelectric component, the output from the piezoelectric component may require pre-processing to ensure a desired analogue signal is produced. One example of a pre-processing step may be to reduce high frequency noise generated by the piezoelectric component from the analogue signal. Pre-processing step 420 may occur at the sensor package 28 or on the data processing device 27.

Subsequent to the pre-processing step 420, a conversion of the signal from an analogue signal to a digital signal is performed in step 430. This analogue to digital conversion may occur at the sensor package 28 or on the data processing device 27.

The digital signal is then processed in step 440 to reduce noise and to time stamp the sensor readings. Step 440 may comprise converting the acceleration vector generated by the accelerometer into a norm of the acceleration vector, i.e., the acceleration vector is converted to a strictly positive length in a single direction. This provides several advantages, including a reduced storage space for storing the vector data and an invariance to accelerometer orientation. Other filters are envisaged, in combination with the above or independently, steps to ensure that the filtered acceleration vector signal is invariant to gravity or orientation of the sensors. In a preferred embodiment, any of the preceding filtering steps are performed locally to the wearable sensors.

Step 440 may further comprise, in combination with the above or independently, applying a low pass filter to remove the acceleration vector resulting from the gravitational force on the accelerometer. This may be achieved by removing slow or unchanging acceleration vectors from a differential of the acceleration vector. This advantageously allows the removal of the noise resulting from gravitational forces.

A key understanding of the present disclosure is that of the need to capture a signal that is most likely to contain an indication of a stroke occurring in the user's brain. Given the difficulty in detecting other biological signals that may be indicative of this occurring, the current disclosure is focused on the detection of a signal from the body's central nervous system that indicates a change in the operation of the brain. In an embodiment where the sensors used to capture this signal include accelerometers, and therefore an acceleration vector based signal capturing movements of the body, it is necessary to filter signals resulting from movements of the human body that are not a direct consequence of the signals from the brain, e.g., they are only indirect outcomes of the electrical signals reaching muscles. Examples of movements that may be filtered include movements that are only an indirect consequence of signals from the nervous system, e.g., when walking along, electrical signals may stimulate the arms to swing forwards and backwards to ensure balance. However, the downward swing of the arms during walking may be the consequence of gravity and the mechanics of the body, rather than the stimulation of any muscles. Consequently, where possible, these movements should be identified and removed from the acceleration vector generated by the accelerometer(s).

Therefore, signals that should be filtered in order to provide the clearest signal of central nervous system activity may include: passive limb mechanics, other biological signals, such as heart function, tremors, or other involuntary muscular movements.

The sensor data is then formatted according to a defined data structure in step 445 for transmission to control device 30. Finally, in step 450, wearable sensor 20 transmits the formatted sensor data to control device 30 using wireless networking interface 34.

Figure 4B:
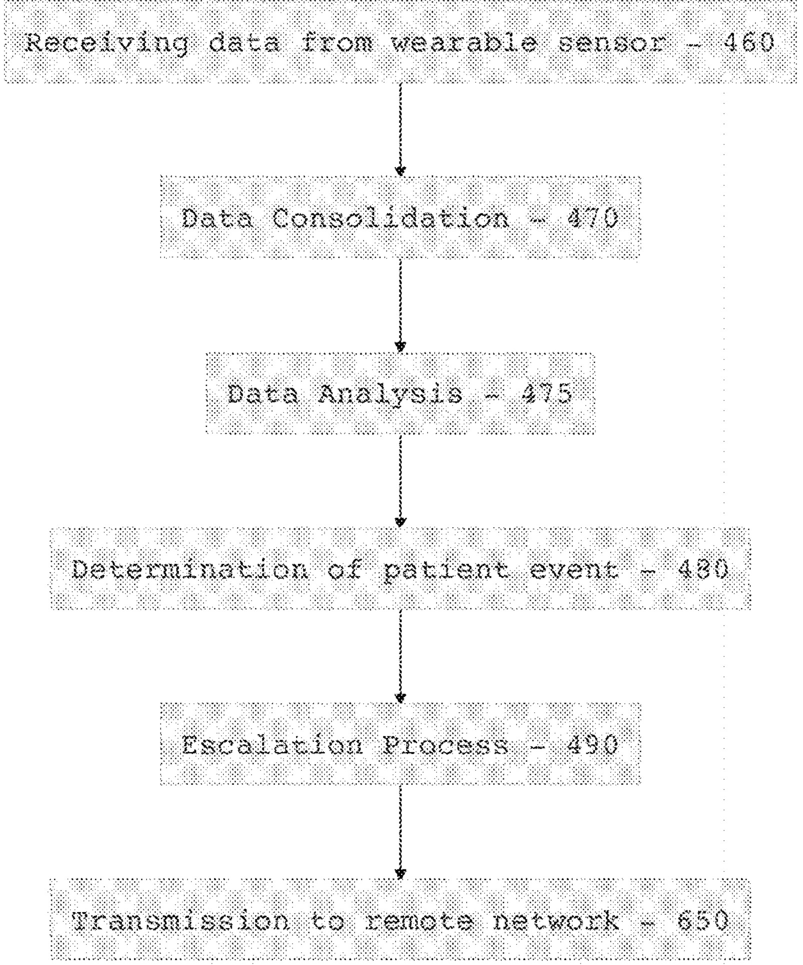

FIG. 4*b* shows an embodiment of the process flow for control device 30. The process flow shown in FIG. 4*b* may be executed in a continuous loop or periodically. Where the process is executed periodically, an energy saving mode may be employed between executions to minimise battery usage.

In step 460, the mobile device receives the formatted sensor data from wearable sensor 20. The received sensor data is then consolidated, in step 470, with existing data previously received from wearable sensor 20 as well as any other wearable sensors transmitting sensor data to control device 30. In one embodiment, the data is stored in a local database stored on control device 30. In one embodiment, the system implements 'chunking' of the formatted sensor data, which comprises break the data into chunks, each chunk comprising a header which indicates some parameters (e.g. the time stamp for the recorded signal data, size etc.) This allows each data chunk to resynchronise the mobile device to the clocks of wearable sensors.

In step 475, data analysis is performed on the sensor data by control device 30. A determination of a patient condition, such as an on-going stroke condition, is then made in dependence on the data analysis 475. This comprises the determination that a probability of a patient condition existing based on the sensor data has exceeded a critical threshold. The process of steps 475 and 480 are described in more detail below and in reference to FIG. 8 and FIG. 9. Upon a determination of a patient condition, escalation process 490 is triggered. Escalation process 490 is described below and in relation to FIG. 6 and FIG. 7. Once escalation process 490 is complete and the patient has been unable to cancel the escalation of the patient condition, control device 30 contacts network point 35 via network interface 34 in step 650 to request emergency service for handling of the patient condition. In one embodiment, mobile device may communicate at least one of a patient condition, a GPS location of the mobile device, a patient ID, a patient medical history, a recent sensor data report, etc.

It should be noted that step 475 and subsequent steps may be executed as a directly subsequent step to step 460. Alternatively, step 475 and subsequent steps may be executed in an independent loop that is triggered independently by e.g. a periodic timing interrupt.

Figure 5A:
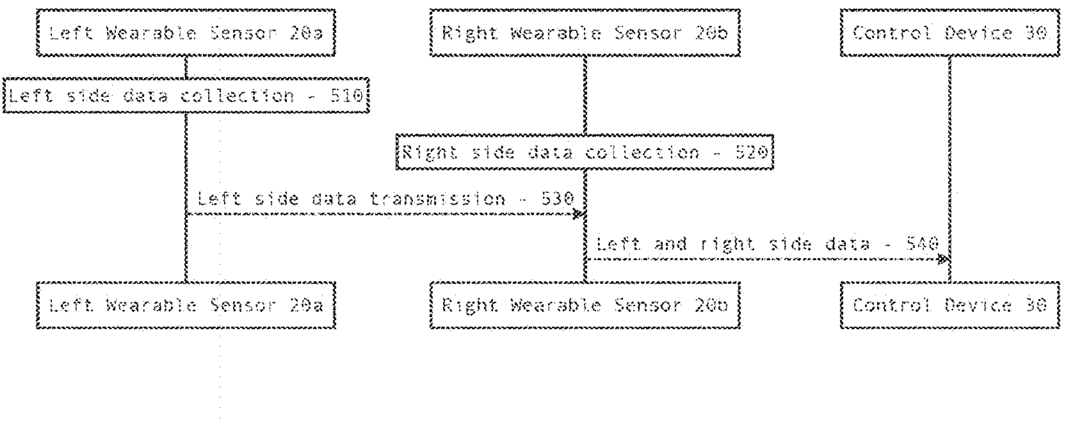
FIG. 5*a* and FIG. 5*b* are sequence diagrams showing data-transmission order between a first and second wearable sensor device and a control device.

In the present description, multiple wearable sensors are used to collect data. FIG. 5*a* shows a flow for collecting the data from more than one wearable sensor at control device 30. In steps 510 and 520, sensor data from a wearable sensors 20*a* positioned on a left side of the body and wearable sensor 20*b* position on a right-hand side of the body is collected. In step 530, sensor data from wearable sensor 20*b* is transmitted to wearable sensor 20*b* via wireless interface 34. Once the sensor data from wearable sensor 20*a* is received at wearable sensor 20*b*, the sensor data from wearable sensor 20*a* is combined with the sensor data from wearable sensor 20*b* (collected previously in step 520) and transmitted to control device 30 in step 540.

Figure 5B:
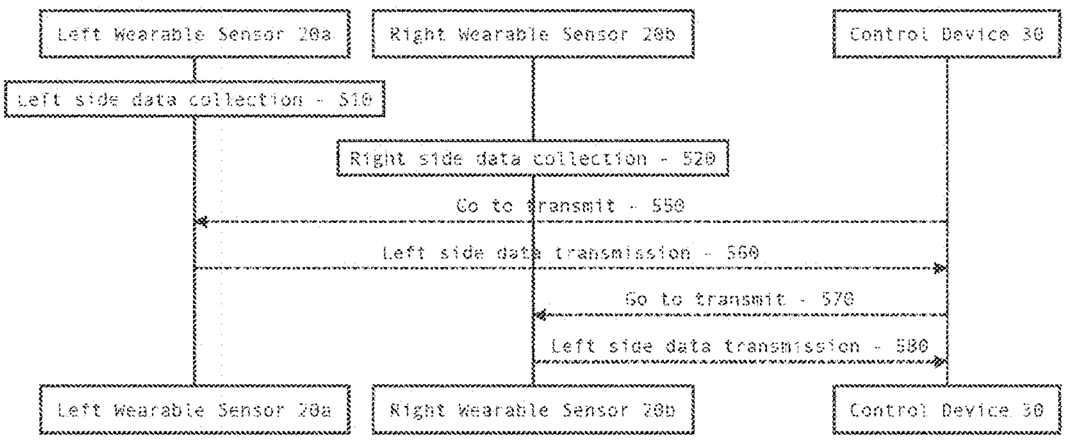

In an alternative embodiment to that shown in FIG. 5*a*, FIG. 5*b* shows an alternative flow for collecting the data from more than one wearable sensor at control device 30. In steps 510 and 520, sensor data from a wearable sensors 20*a* positioned on a left side of the body and wearable sensor 20*b* position on a right-hand side of the body is collected. In step 550, control device 30 instructs wearable sensors 20*a* via wireless network interface 34 to send sensor data collected by wearable sensor 20*a* to control device 30. In step 560, wearable sensor 20*a* sends the collected data to control device 30 via wireless network interface 34. In step 570, control device 30 instructs wearable sensors 20*b* via wireless network interface 34 to send sensor data collected by wearable sensor 20*b* to control device 30. In step 580, wearable sensor 20*b* sends the collected data to control device 30 via wireless network interface 34.

Figure 6:
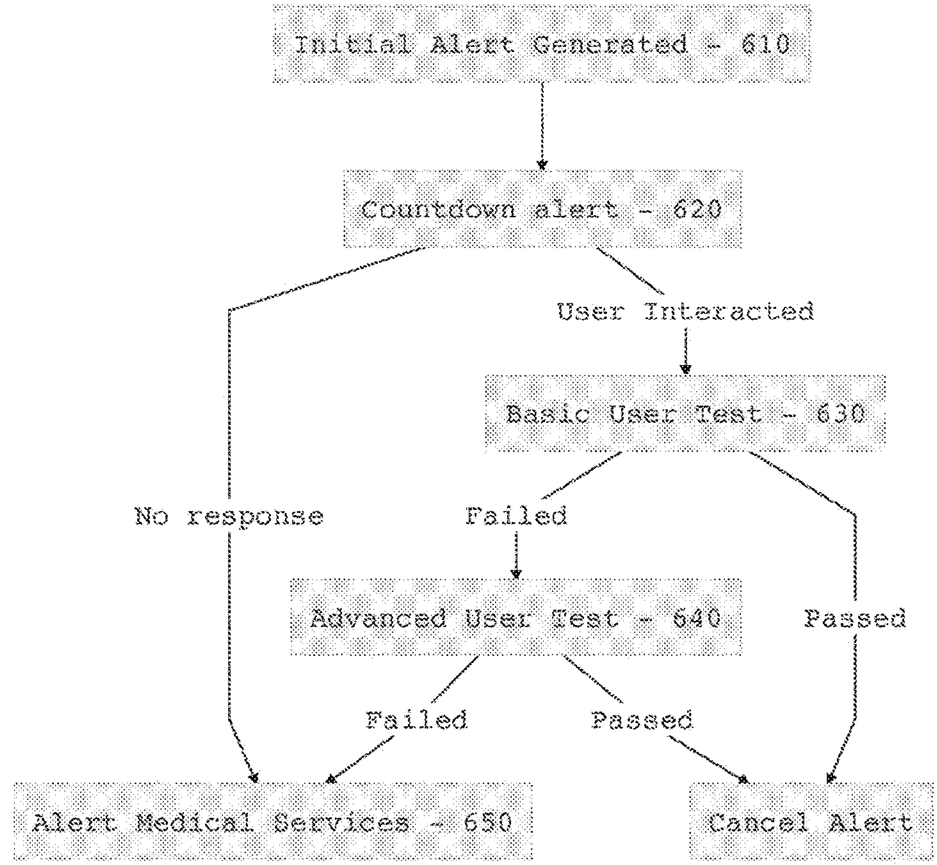
FIG. 6 is a process flow diagram showing execution flow of the control device 30.

FIG. 6 shows an embodiment of escalation process 490 shown in FIG. 4*b*. Once a threshold for the probability of a patient condition being present has been exceeded, an embodiment of the description provides a process for testing the patient to determine if the patient is actually suffering from symptoms of the condition or whether the sensor data has merely resulted in a 'false positive'. Escalation process 490 comprises the following steps:

In step 610, control device 30 begins the escalation process when the probability of a patient condition being present has been exceeded. In an embodiment of the invention, one or more user tests will be employed during a testing process to determine the user's physical and mental state. The term 'user' and 'patient' may be used interchangeably.

In one embodiment, the testing process comprises a countdown alert 620 presented to the user on the display of control device 30. The countdown alert 620 may comprise a simple countdown alert showing a countdown in seconds before which control device 30 will move to step 650 to alert the medical services. The user has the option of cancelling the countdown at any time. If the user fails to respond to the countdown alert, control device 30 will move straight to step 650 to alert medical service. Where the patient cancels the countdown by performing the required cancellation task (e.g. pressing a CANCEL button), the patient is presented with the option to reset the escalation process. Alternatively, the user may be presented with the option of moving straight to step 650 to alert medical service if the patient feels that something is still wrong. In one embodiment, the user cannot cancel the countdown alert until all of the user tests are successfully completed. In one embodiment, a two part countdown is used. Countdown 1 is a short term countdown (e.g. less than 60 seconds) and may be cancelled by the user. Countdown 2 is a longer term countdown (e.g. longer than 60 seconds) that can only be cancelled by successfully completing all of the user tests.

In one embodiment, the testing process comprises a basic user test 630 presented to the user on the display of control device 30. The basic user test may comprise one or more physical tests. A physical test may comprise a request that the patient move one or more of his or her limbs in a prescribed manner, e.g., move one hand or leg, move opposite hands or legs in sequence or simultaneously, clap the hands, stand up, jump, raise one or more knees to the patient's chest etc. A physical test is intended to perform one or more functions. Where motion sensor data indicates that one or more limb or side of the body appears to have limited movement, a physical test may be intended to provide data that can be used to discount the possibility that the patient is suffering from any form of paralysis, e.g., standing up or waving each hand in turn. Alternatively, where the motion sensor data indicates that a general asymmetry exists in the patient's movements, a physical test may be intended to provide data that can be used to provide clear data on the symmetry of the patient's present movements, e.g., where a patient is wearing a wearable sensor on each wrist, a hand clap should provide a clearly symmetrical signal from each wearable sensor as long as the patient has a full range of movement in both arms. In the embodiment of FIG. 6, if the user fails the basic user test 630, control device 30 presents a further test to the patient. In alternative embodiments, control device 30 will move straight to step 650 to alert medical service if the patient fails the basic user test 630. Where the patient passes basic user test 630, the patient is presented with the option to reset the escalation process.

Alternatively, the user may be presented with the option of proceeding with further tests or moving straight to step 650 to alert medical service if the patient feels that something is still wrong. It should be understood that the user tests described in the present description may be presented to the user in any combination or order deemed to produce the most reliable result.

In one embodiment, the testing process comprises an advanced user test 640 presented to the user on the display of control device 30. The advanced user test may comprise one or more mental tests. A mental test comprises a request that the patient complete one or more mental tests intended to demonstrate that the user is capable of thinking clearly and rationally, e.g. a mental arithmetic test, a verbal reasoning test, a facial or general image recognition test, a vocalisation test, etc. As with the basic user test 630, if the user fails the advanced user test 640, control device 30 may presents a further step to the patient before moving to step 650. In alternative embodiments, control device 30 will move straight to step 650 to alert medical service if the patient fails the advanced user test 640. Where the patient passes advanced user test 640, the patient is presented with the option to reset the escalation process. Alternatively, the user may be presented with the option of proceeding with further tests or moving straight to step 650 to alert medical service if the patient feels that something is still wrong.

Figure 7:
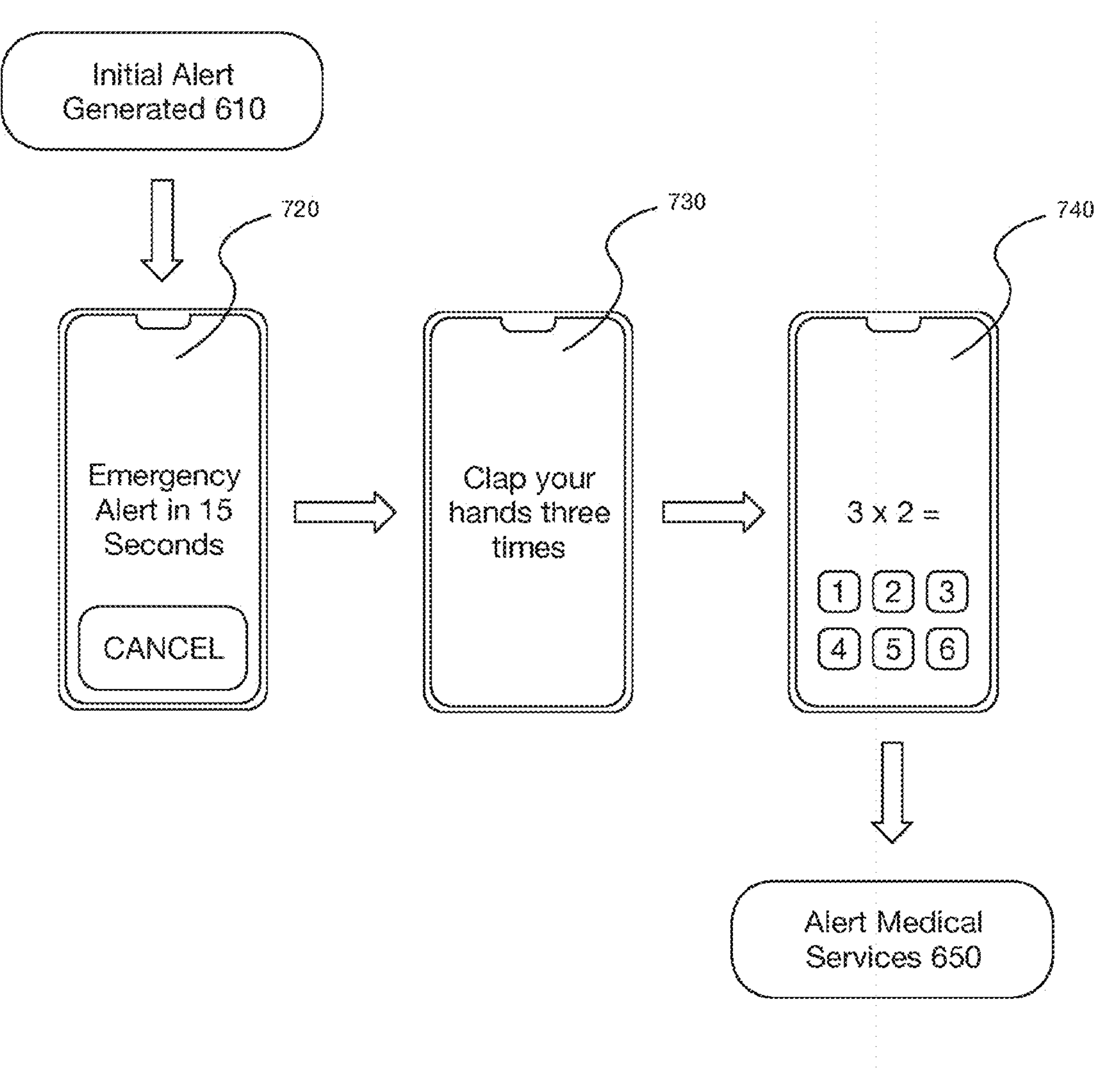
FIG. 7 is an alternative process flow diagram showing execution flow of the control device 30.

FIG. 7 shows an alternative sequence of user tests to that shown in FIG. 6. In FIG. 7, step 720 comprises a countdown alert to provide the patient the opportunity to cancel the escalation where he or she still believe that no patient condition exists. Where no response is received, the alert is escalated immediately. In one embodiment, the countdown continues until all the subsequent tests are passed. Subsequent to the countdown alert, step 730 comprises a basic user test comprising a request that the user clap his or her hands three times. Finally, step 740 comprises an advanced user test as described above. In the embodiment of FIG. 7, the advanced user test is a mental arithmetic test to assess the mental ability of the patient.

In one embodiment, a user test may comprise a vibration prompt only. This may determine where a user is unable to sense a vibration due to an ongoing stroke. In one embodiment, a flashing light is used as a control to the vibration test.

Figure 8A:
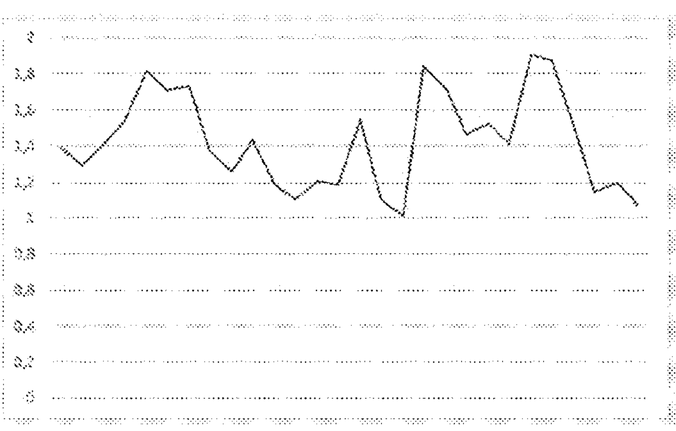
FIGS. 8*a*-8*c* are example motion sensor signal graphs of the stroke detection apparatus.
Figure 8B:
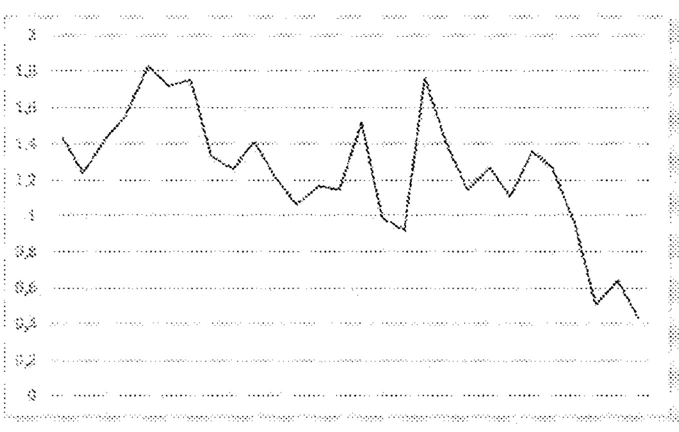
Figure 8C:
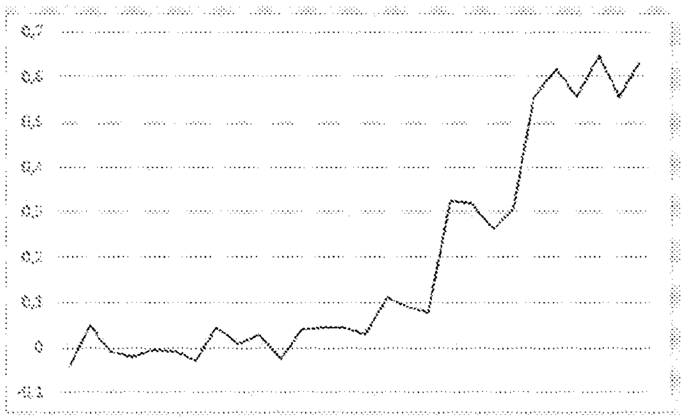

FIG. 8*a*-*c* show an example sensor data set from the present apparatus where wearable sensors 20*a* and 20*b* comprise accelerometers generating motion sensor data. FIG. 8*a* shows an example motion sensor data generated by wearable sensor 20*a* secured to a left limb of the patient's body over the period of an hour. FIG. 8*b* shows an example motion sensor data generated by wearable sensor 20*b* secured to a right limb of the patient's body over the same time period to that of FIG. 8*a*. In FIG. 8*c*, a differential between the motion sensor data of FIG. 8*a* and the motion sensor data of FIG. 8*b* is shown. Where the wearable sensors 20*a* and 20*b* are secured symmetrical to the patient's body, the differential between the motion sensor data from the respective wearable sensors 20*a* and 20*b* may show a low frequency motion asymmetry between the limb of the left side of the body and the limb of the left side of the body to which the wearable sensors are respectively secured. In FIG. 8*a*, a growing asymmetry is shown between the limbs of the left and right side of the patient as the hour progress.

Figure 9:
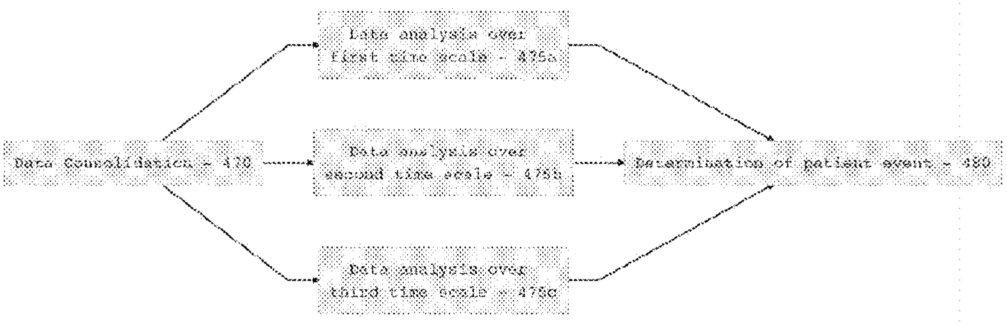
FIG. 9 is an alternative process flow diagram showing execution flow of the control device 30.

FIG. 9 shows an embodiment extending the embodiment of FIG. 4*b*. In the embodiment of FIG. 9, data analysis step 475 is split into a plurality of data analysis steps 475*a*, 475*b*, etc that may be performed in series or in parallel. In this embodiment, the data stored on control device 30 may be analysed in a different way for each of the plurality of data analysis steps.

Figure 10:
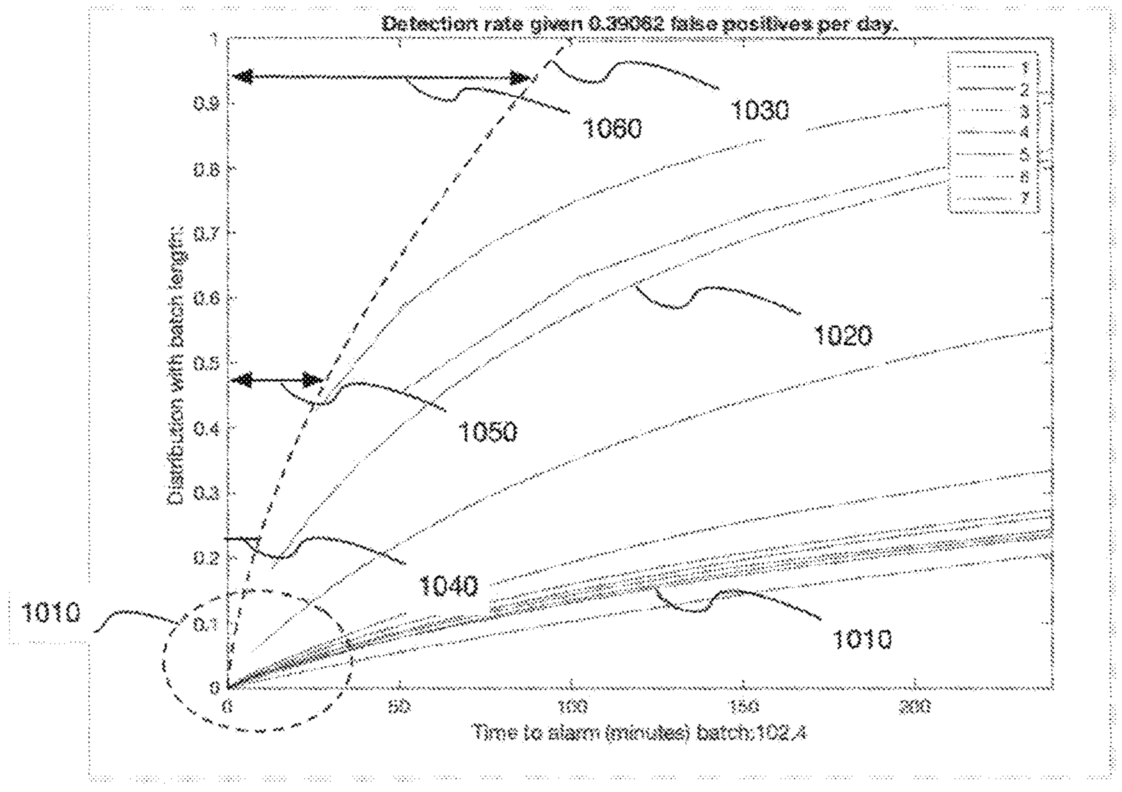
FIG. 10 shows the time it takes an embodiment of the system to detect a stroke given specific configurations.

FIG. 10 shows results for an embodiment using a plurality of plurality of data analysis steps 475 configured to analyse the motion sensor data over different time periods (shown by lines 1010 and 1020). In such an embodiment, analysing the motion sensor data over a short period (e.g. line 1010) allows the possibility of find strokes quickly and relatively soon after they occur. However, in order to minimise false alarms, a short period analysis requires a narrow detection threshold, e.g., an analysis over a shorter time period is more likely to have a degree of noise that might trigger a false positive. Therefore, the range of acceptable positive values needs to be narrow, and a high threshold should be met before a stroke detection signal is generated. However, a high threshold may result in poor detection rates when the device is used over a longer period of time. In order to compensate for this, one embodiment provides the use of a data analysis step run in parallel with the short period analysis that analyses the motion sensor data over a longer period of time (e.g. line 1010). Analysing the motion sensor data over a longer period of time allows better detection rates, but necessarily incurs a longer delay before a stroke can be detected. In an example where the motion sensor data is analysed over a period of an hour, a very high detection rate of almost 100% detection rate may be achieved, but an hour's delay is introduced to the detection, which could make a significant difference to the stroke victim's outlook. A fused method (shown by line 1030) can get the benefits of all methods.

In one embodiment, the stroke detection apparatus may operate in multiple modes, varying the fidelity, data rate, resolution, or number of dimensions of the motion sensor data stored on the device. In an embodiment comprising two operating modes, the stroke detection apparatus may be configured to operate in a first mode when a possibility of an occurring stroke is determined by the stroke detection apparatus to be below a first threshold. In the first mode, the motion sensor data is stored at a first fidelity, i.e., the sample rate, sample size, bit rate, number of dimensions, or equivalent used to store the motion sensor data is set to a first value. Upon determination by the stroke detection apparatus that a risk of an ongoing stroke has risen above the first threshold, the stroke detection apparatus may be configured to operate in a second mode. In the second mode, the motion sensor data is stored at a second fidelity higher than the first fidelity, i.e., the sample rate, sample size, bit rate, number of dimensions, or equivalent used to store the motion sensor data is set to a second value, higher than the first value. This allows more detailed and more concise monitoring of the patient movement for periods of time when the patient stroke risk is determined to be high, while allowing improved storage and/or reduce power consumption by the device while the patient stroke risk is determined to be low.

In another embodiment, the stroke detection apparatus may be configured to operate in a first mode and/or second mode (as described above), as well as a third mode. The stroke detection apparatus may be configured to operate in a third mode when the stroke detection apparatus is monitoring the user for a specific movement, e.g., where the stroke detection apparatus has prompted the user to perform a specific movement or gesture in order to pass a test. In the third mode, the motion sensor data is stored at a third fidelity higher than the first and/or second fidelity, i.e., the sample rate, sample size, bit rate, number of dimensions, or equivalent used to store the motion sensor data is set to a third value, higher than the first and or second values. The third mode allows the stroke detection apparatus to accurately capture the user's movements for a short period of time in sufficient fidelity that particular gestures can be captured. In some embodiments, a first mode and/or second mode stores motion sensor data in just a single dimension, while the third mode stores motion sensor data in a plurality of dimensions. This may allow clearer determination of particular patient movements.

In a one embodiment, the above apparatus is used in a rehabilitation context rather than a stroke detection context. By indirectly monitoring the patient's nervous system signals in the same manner as described above for detecting a stroke, the patient's recovery from a stroke can be tracked and rehabilitation guidance can be provided. Stroke rehabilitation strives to enable a patient to regain as much of the functions damaged by the stroke as possible and to aid the stroke victim to obtain as much functional independence as possible. Stroke rehabilitation is essential for the final functional outcome after stroke and the costs associated with the long-time disability following a stroke. In one configuration, the apparatus is configured to: 1) Monitor and quantify the rehabilitation progress over time; and 2) Provide an active support to the stroke victim throughout the rehabilitation.

The process of monitoring and quantifying the rehabilitation progress may comprise reporting the correlation between accelerometer data (i.e. patient movement data) from the wearable sensors and a physiotherapist assessment of arm function before and after rehabilitation. Accelerometer data from the wearable sensors, and corresponding relevant movement data is presented in the app for the patient, and for the professional rehabilitation team.

The process of providing an active support to the stroke victim throughout the rehabilitation may comprise generating exercise instructions for the patient in dependence on the accelerometer data from the wearable sensors. In one embodiment, the difficult, duration, and timing of the exercise instructions is dependent on the patient's movement data, i.e., where a patient appears to have had limited body movement over a period of time, against rehabilitation recommendations, the system is configured to instruct the user to perform more regular and more intensive movement exercises.

The invention claimed is:

1. A stroke detection apparatus comprising:

at least one wearable sensor configured to be worn by a user and configured to generate a movement data of the user, the at least one wearable sensor comprising, a sensor package configured to measure an acceleration of the user, a data processing device comprising a system memory, and a power source configured to power the data processing device, the sensor package configured to transmit the movement data to the data processing device, the data processing device configured to cause the stroke detection apparatus to:

receive the movement data, filter the movement data to remove acceleration resulting from gravitational force, process the movement data to determine a probability of a user stroke, the probability indicates a percentage chance of stroke occurrence, and store the movement data on the system memory at a fidelity dependent on the probability of the user stroke, wherein the fidelity of the stored movement data comprises at least one of a sample rate, a sample size, or a bit rate of the movement data, wherein when the probability of the user stroke is determined to be below a first probability threshold, the stroke detection apparatus is further configured to operate in a first mode where the movement data is stored at a first fidelity, wherein when the probability of the user stroke is determined to be above the first probability threshold, the stroke detection apparatus is configured to operate in a second mode where the movement data is stored at a second fidelity, wherein the first probability threshold is a determined percentage chance of stroke occurrence, and wherein the second fidelity is higher than the first fidelity, to reduce power consumption from the power source in the first mode.

2. The stroke detection apparatus of claim 1, wherein the stroke detection apparatus is configured to generate one or more user tests once a threshold for the probability of the user stroke has been exceeded, wherein the one or more user tests comprises at least one of a reaction time test, an arithmetic test, a reading test, a comprehension test, a memory test, or a user response test.

3. The stroke detection apparatus of claim 2, wherein the stroke detection apparatus is configured to generate a stroke escalation signal where the user fails the one or more of the user tests.

4. The stroke detection apparatus according to claim 1, wherein the stroke detection apparatus is configured to operate in the first mode wherein the processed movement data is limited to a single dimension, and wherein the stroke detection apparatus is configured to operate in the second mode wherein the processed movement data is 3-dimensional, and determine the probability of the user stroke in dependence on the processed movement data according to the first mode and determine a user gesture in dependence on the processed movement data according to the second mode.

5. The stroke detection apparatus according to claim 1, wherein the stroke detection apparatus is configured to operate in a third mode when the stroke detection apparatus is monitoring the user for a specific movement.

6. The stroke detection apparatus according to claim 5, wherein the stroke detection apparatus is configured to operate in the third mode when the stroke detection apparatus has prompted the user to perform the specific movement in order to pass a test.

7. The stroke detection apparatus according to claim 5, wherein the movement data of the user from the at least one wearable sensor is stored at a third fidelity in the third mode, wherein the third fidelity is higher than a first fidelity and a second fidelity.

8. A method for generating a stroke detection signal comprising:

generating, using at least one wearable sensor device configured to be worn by a user, a movement data of the user;

transmitting the movement data to a processing device being powered by a power source;

receiving the movement data at the processing device;

filtering the movement data to remove acceleration resulting from gravitational force;

processing the movement data at the processing device to determine a probability of a user stroke, the probability indicates a percentage chance of stroke occurrence, the method further comprising, storing the movement data at a fidelity dependent on the probability of the user stroke, wherein the fidelity of the stored movement data comprises at least one of a sample rate, a sample size, or a bit rate;

in a first operating mode, storing the movement data at a first fidelity on a system memory of the data processing device when the probability of a user stroke is determined to be below a first threshold; and in a second operating mode, storing the movement data at a second fidelity on the system memory when the probability of a user stroke is determined to be above the first threshold, wherein the first probability threshold is a determined percentage chance of stroke occurrence, and wherein the second fidelity is higher than the first fidelity, to reduce power consumption from the power source in the first operating mode.

* * * * *